United States Patent [19]

Giesselmann et al.

[11] Patent Number: 4,481,220

[45] Date of Patent: Nov. 6, 1984

[54] WATER-SOLUBLE COMPOSITION FOR FORMING AN AQUEOUS ISOTONIC NITROGLYCERINE SOLUTION AND THE NITROGLYCERINE SOLUTION FORMED

[75] Inventors: Ewald Giesselmann; Ulrich Münch, both of Monheim, Fed. Rep. of Germany

[73] Assignee: Sanol Schwarz GmbH, Fed. Rep. of Germany

[21] Appl. No.: 438,887

[22] PCT Filed: Mar. 12, 1982

[86] PCT No.: PCT/DE82/00054

§ 371 Date: Sep. 29, 1982

§ 102(e) Date: Nov. 8, 1982

[87] PCT Pub. No.: WO82/03172

PCT Pub. Date: Sep. 30, 1982

[30] Foreign Application Priority Data

Mar. 13, 1981 [DE] Fed. Rep. of Germany ....... 3109783

[51] Int. Cl.$^3$ .............................................. A61K 31/04
[52] U.S. Cl. .................................................... 424/349
[58] Field of Search ......................................... 424/349

[56] References Cited

U.S. PATENT DOCUMENTS 3,789,119  1/1974  Fusari et al. ................... 424/349

OTHER PUBLICATIONS

Merck Index, (1976), 9th Ed., p. 1017.

Primary Examiner—Stanley J. Friedman
Attorney, Agent, or Firm—Charles A. Muserlian

[57] ABSTRACT

Preparation that can be dissolved in water to form an approximately isotonic nitroglycerine solution having a concentration of approximately 1 mg of nitroglycerine/ml of solution.

7 Claims, No Drawings

WATER-SOLUBLE COMPOSITION FOR FORMING AN AQUEOUS ISOTONIC NITROGLYCERINE SOLUTION AND THE NITROGLYCERINE SOLUTION FORMED

The invention relates to a preparation that can be dissolved in water to form an approximately isotonic nitroglycerine solution having a concentration of approximately 1 mg of nitroglycerine/ml of solution, and to an approximately isotonic aqueous nitroglycerine solution having a content of approximately 1 mg of nitroglycerine/ml of solution.

It should be possible to manufacture the approximately isotonic nitroglycerine solution having a concentration of approximately 1 mg of nitroglycerine/ml of solution from the preparation according to the invention by dissolving the preparation in water. This nitroglycerine solution could be used for infusions. The concentration of 1 mg of nitroglycerine/1 ml of solution would offer the user a simple basis for calculating amounts infused and further dilutions. Further advantages would be that patients would be subjected to relatively small infusion volumes and that, in the case of intensive treatment, infusion piston pumps would rarely need to be changed.

TABLE 1

| | | Known nitroglycerine solutions | | | |
|---|---|---|---|---|---|
| | | Solvent | | | |
| No. | Nitroglycerine concentration (mg/ml) | | After dilution with water to 1 mg nitroglycerine/ml solution | Remarks | Literature |
| 1 | 1 | approx. 100% ethanol | — | a,b | Rote Liste 1980 |
| 2 | 5 | approx. 100% ethanol | 20% ethanol + 80% water | a,b | " |
| 3 | 5 | approx. 100% ethanol | 20% ethanol + 80% water | a,b | " |
| 4 | 3.1 | 1,2-propylene glycol + (unspecified) ethanol | ? | a,b | " |
| 5 | 0.63 | 1,2-propylene glycol + (unspecified) ethanol | impossible | c | " |
| 6 | ? | approx. 100% ethanol | | a,b | Trissel, "Handbook of Injectable D ugs" 2nd Edition, 1980 |
| 7 | 0.15 | water | impossible | c | Trissel, "Handbook of Injectable D ugs" 2nd Edition, 1980 |
| 8 | 10 | approx. 100% ethanol | 10% ethanol + | a,b,d | Gstirner, "Grundstoffe und Verfahren der Arzneibereitung" P. 387, Stuttgart 1960 |
| 9 | 10 | 90% ethanol + 10% water | 9% ethanol + 91% water | a,b,d | Martindale p. 1646, London |
| 10 | 10 | approx. 100% ethanol | 10% ethanol + 90% water | a,b,d | Dean and Baun, Am. J. Hospital Pharm. 32 (1975) 1036 |
| 11 | 0.4 | 4% ethanol + 96% water | — | c | Dean and Baun, Am. J. Hospital Pharm. 32 (1975) 1036 |

Remarks:
a: toxicologically undesirable; see, for example, Kuhn and Loogen, Internist, 19 (1978) 97-106
b: Not isotonic; an isotonic solution contains only 1.28% ethanol or 2.0% propylene glycol
c: concentration too low
d: Risk of nitroglycerine precipitation

TABLE 2

| | | Dissolution of tablets (NG = Nitroglycerine) | | | | |
|---|---|---|---|---|---|---|
| No. | Tablets (mg NG/ tablet) | Solution solution medium | NG concentration (mg/ml) | NG total amount (mg)/ mixture | Remarks | Literature |
| 1 | 0.6 | water | 0.15 | ? | c | Flaherty et al., Circulation, 51 (1975) 132 |
| 2 | 0.4 | 0.9% NaCl + 99.1% water | 0.4 | 8 | c | Kaplan et al., Anesthesiology, 45 (1976) 14 |
| 3 | 0.6 | water | 1 | ? | hypertonic approx. 17% solids in case of 100 mg tablet | Cottrell and Turndorf, Am. Heart J., 96 (1978) 550 |
| 4 | | water | 0.4 | ? | c | Sturek et al., Am. J. Hosp. |
| 5 | | 5% dextrose + | 0.4 | ? | c | |

TABLE 2-continued

| | | Dissolution of tablets (NG = Nitroglycerine) | | | | |
|---|---|---|---|---|---|---|
| No. | Tablets (mg NG/ tablet) | Solution solution medium | NG concentration (mg/ml) | NG total amount (mg)/ mixture | Remarks | Literature |
| 6 | 0.4 | 95% water<br>0.9% NaCl + 99.1% water | 0.4 | ? | c | Pharm., 35 (1978) 537 |
| 7 | 0.4 | 0.9% NaCl + 99.1% water | 0.08 | 87.2 | c | McNiff et al., Am. J. Hosp. Pharm. 36 (1979) 173 |
| 8 | 0.4 | (a) 0.9% NaCl + 99.1% water +<br>(b) 5% dextrose + 95% water<br>(a):(b) = 10:240 or 20:230 | 0.03 | 8 | c | |
| 9 | 0.4 | 0.9% NaCl + 99.1% water | 1 | 40 | hypertonic approx. 25% solids in case of 100 mg tablet | Swerling, Hosp. Pharm., 14 (1979) 420 |

TABLE 3

| | | Dissolution of adsorbate (NG = Nitroglycerine) | | | |
|---|---|---|---|---|---|
| | | Solution | Solvent | | |
| No. | Lactose adsorbate (% NG) | NG concentration (mg/ml) | | after dilution with water to 1 mg NG/ml | Remarks | Literature |
| 1 | 10 | 10 | 100% ethanol | 10% ethanol + 90% water | a,b,c of Table 1 | Fung and Rhodes. Am. J. Hosp. Pharm., 32 (1975) 139 |
| 2 | 10 | 10 | 100% ethanol | 10% ethanol + 90% water | a,b,c of Table 1 | Ward et al., Drug Intell. Clin. Pharm., 13 (1979) 14 |
| 3 | 10 | 0.4 | 0.9% NaCl + 99.1% water | impossible | | McNiff et al., Am. J. Hosp. Pharm., 36 (1979) 173 |

As can be seen from Table 1, nitroglycerine solutions are already known. These known nitroglycerine solutions have, however, a nitroglycerine concentration of less than 1 mg/ml or have (optionally after dilution to a nitroglycerine concentration of 1 mg/ml) a toxicologically undesirably high content of organic solvent and a hypertonic value. In this connection, reference is made to Kuhn and Loogen, "Die Wirkung von Alkohol auf das Herz einschliesslich der Alkoholcardiomyopathie", *Internist* 19 (1978) 97–106. Diluting solutions having a nitroglycerine concentration of 10 mg/ml at least, may lead to a dangerous nitroglycerine precipitation; see Martindale, "The Extra Pharmacopoeia", 27th Edition, p. 1647, London. On the danger of nitroglycerine droplet formation, see also Kutkiewicz and Kowalski, *Chem. Abs.*, 74 (1971) 170, reference 128 368 w.

As shown in Table 2, nitroglycerine solutions have also already been manufactured by dissolving tablets. The nitroglycerine solutions obtained however also have a nitroglycerine concentration of less than 1 mg/ml or (as a consequence of the high ratio of bulk material:nitroglycerine) a hypertonic value. A known adsorbate of 10% nitroglycerine on lactose has a relatively favourable ratio of bulk material:nitroglycerine (Table 3). In that case, however, the following is to be noted. It is not by chance that Fung and Rhodes and also Ward et al propose the extraction of the adsorbate with ethanol in order to manufacture solutions from which nitroglycerine concentrations of 1 mg/ml can be obtained. Indeed, nitroglycerine has a low saturation concentration in water, in solubilisers customarily used for parenteral administration and in aqueous solutions containing such solubilisers, ethanol still proving to be best; see Table 4.

TABLE 4

| Saturation concentration of nitroglycerine | | |
|---|---|---|
| Solvent | Saturation concentration of nitroglycerine (mg/ml) | Literature |
| water | 1.73 | Ullman, vol. 16, p.70, 1965 |
| water + 5% Tween 20 | 4.5 | Gstirner, p. 955, 1960 |
| water + 10% Tween 20 | 6.4 | Gstirner, p. 955, 1960 |
| ethanol | 540 | Ullmann, vol. 16, p.70, 1965. |
| 1,2-propylene glycol | approx. 80 | — |

If nitroglycerine is introduced into water on a water-soluble solid carrier, the water-soluble carrier dissolves, and a high local nitroglycerine concentration which is above its saturation concentration occurs. The nitroglycerine collects in droplets or drops with the result that there is a danger of an explosion while the nitroglycerine drops are slowly dissolving in the supernatent solution (Comparison Example 1). It is therefore not possible to use this procedure for the manufacture of nitroglycerine solutions on an industrial scale.

Despite the poor solubility of nitroglycerine in solubiliers customarily used for parenteral administration and in aqueous solutions containing such solubilisers, surprisingly it has now been found that, according to the invention, it is possible to provide a preparation that can be dissolved in water to form an approximately isotonic nitroglycerine solution having a concentration of approximately 1 mg of nitroglycerine/ml of solution without the separation of nitroglycerine droplets, by providing a small amount of a solubiliser customarily used for parenteral administration in conjunction with a solid nitroglycerine carrier.

According to the invention, therefore, there is provided a preparation that can be dissolved in water to form an approximately isotonic nitroglycerine solution having a concentration of approximately 1 mg of nitroglycerine/ml of solution, which comprises
(a) nitroglycerine,
(b) a solubiliser customarily used for parenteral administration, and
(c) as a solid nitroglycerine carrier, a substance which is customarily used in isotonic basic solutions and renders them isotonic having a weight ratio of nitroglycerine:solubiliser of from 0.1:1 to 10:1,
and having an amount of carrier which supplements the total amount of all the substances in an amount of preparation containing approximately 0.1 g of nitroglycerine to the equivalent corresponding to approximately 0.90 g of sodium chloride for isotonicity.

The amount of carrier therefore supplements the total amount of all the substances in an amount of preparation containing 0.1 g of nitroglycerine to the isotonicity equivalent corresponding to approximately 0.90 g of sodium chloride.

The isotonicity equivalent ensures that when an amount of preparation containing approximately 0.1 g of nitroglycerine is dissolved to form an aqueous solution having a content of approximately 1 mg of nitroglycerine/ml of solution, an approximately isotonic nitroglycerine solution is obtained. For the manufacture of isotonic solutions, it is customary in the field of medicaments to express the amount of individual constituents of a medicament in sodium chloride equivalents; see, for example, Gstirner, "Grundstoffe und Verfahren der Arzneibereitung", Stuttgart 1960, p. 204, Table 24.

In respect of the value of 0.1 g of nitroglycerine, values that exceed or fall short of that value by up to 10%, preferably up to 5%, and especially up to 2%, are tolerated according to the invention. In respect of the isotonicity equivalent corresponding to 0.90 g of sodium chloride, deviations that are within the range of from 0.60 to 1.50 g of sodium chloride or that lead to a depression of the freezing point within the range of from 0.51° to 0.63° C. when an amount of preparation according to the invention having a content of approximately 0.1 g of nitroglycerine is dissolved to form an approximately isotonic aqueous nitroglycerine solution having a concentration of approximately 1 mg of nitroglycerine/ml of solution are tolerated according to the invention. In respect of a concentration of 1 mg of nitroglycerine/ml of solution, concentrations that exceed or fall short of that concentration by up to 10%, preferably by up to 5%, and especially up to 2%, are also tolerated according to the invention.

In the case of special embodiments, the weight ratio of nitroglycerine:solubiliser may be from 0.2:1 to 5:1, preferably from 0.3:1 to 3:1, and especially from 0.5:1 to 2:1.

With regard to solubilisation, reference is made, in general, to the following literature, the disclosures of which are incorporated herein: Rohdewald, "Grundlagen der Lösungsvermittlung", Pharm. Z., No. 19 (1971) 673–680; Anschel, "Lösungsmittel und Lösungsvermittler", Pharm. Ind., 27 (1965) 781–787; Fiedler, "Lexikon der Hilfsstoffe für Pharmazie, Kosmetik und angrenzende Gebiete", pages 341 and 342 etc., Aulendorf 1971; Sucker et al., "Pharmazeutische Technologie", pages 283 etc., 551 etc., and 556 etc., Stuttgart 1978; Gstirner, "Einführung in die Verfahrenstechnik der Arzneiformung," p. 271 etc. Stuttgart 1973; and Böhme et al., "Europäisches Arzneibuch", vol. 3, Kommentar, pages 657 etc., Stuttgart 1979.

It is surprising that, preferably, a liquid solubiliser can be used without clumping of a finely particulate preparation according to the invention and loss of its pourability. Molecularly disperse solubilisers can be selected from the following groups:
(a) monovalent and polyvalent, lower and higher alcohols, such as
1,2-propanediol,
1,3-butanediol, and glycerine,
(b) lower and higher ether alcohols, such as
1,2-propylene glycol-1-n-propyl ether (Soluphor CE 5149),
1,2-butylene glycol-1-methyl ether (Soluphor CE 5151),
tetraethylene glycol (Tetraglycol or Glucofurol), and
polyethylene glycol (average molecular weight, for example, from 200 to 600),
(c) lower and higher ethers, such as
isopropylpropylene glycol ether,
diethylene glycol dimethyl ether, and
tetrahydrofurfuryl methyl ether,
(d) esters of monovalent or polyvalent organic acids, such as
ethyl lactate,
glycol monoacetate,
glycol diacetate,
glycol monopropionate,
glycol dipropionate, and
propylene glycol propionate,
(e) monovalent or polyvalent organic acids, such as
lactic acid,
(f) amides of organic acids, such as
dimethylformamide,
dimethylacetamide,
N-($\beta$-hydroxyethyl)lactamide, and
N,N-dimethylmethoxyacetamide,
(g) acetals and ketals, such as
isopropylidene glycerol (glycerol dimethyl ketal), and
glycerine formal,
(h) urea and derivatives thereof, such as
urethane, for example ethylurethane, and
tetraethylurea, and
(i) sulphones, such as
tetrahydrothiophene-1,1-dioxide (Sulfolan).

In addition, colloidally disperse solubilisers selected from the following group can be used:
cellulose derivatives, for example carboxymethylcellulose (cellulose glycolate),
Pluronic,
Tetronic and
castor oil/ethylene oxide condensates (Cremophor).

There come into consideration as nitroglycerine carriers solid substances that are customarily used for the manufacture of basic infusion solutions or isotonic basic solutions. Examples of solutions of that type are 0.9% strength sodium chloride solution, 5% strength glucose solution, Ringer's solution, Ringer's lactate solution and solutions of full electrolytes and mixtures thereof. Examples of nitroglycerine carriers are especially sodium chloride, mannitol, sorbitol, glucose, lactose and levulose and mixtures thereof; see Ahnefeld and Schmitz, "Systematisierung von Infusionslösungen und Grundlagen der Infusionstherapie", Karger-Verlag 1980.

The preparation according to the invention can be manufactured, for example, by mixing the nitroglycerine, solubiliser and nitroglycerine carrier in a volatile solvent and subsequently evaporating off the solvent.

The composition of the preparation according to the invention ensures that it can be dissolved at a temperature of up to 100° C., especially up to 70° C., on an industrial scale, without precipitation of nitroglycerine, to form an approximately isotonic aqueous nitroglycerine solution having a concentration of approximately 1 mg of nitroglycerine/ml of solution.

The solution according to the invention is ready for use and does not require to be diluted further. In this manner, the danger of contamination during dilution and also possible incompatibility between active substance and infusion solution are avoided; see Ahnefeld and Schmitz,
loc. cit., p. 67 and 73. From a toxicological point of view, the complete lack of ethanol in the solution according to the invention is especially advantageous.

The invention is explained in detail below by means of examples and a comparison example.

EXAMPLES 1 TO 4 AND COMPARISON EXAMPLE 1

In each case, a mixture of 0.5 g of nitroglycerine, optionally 0.5 g of solubiliser, and anhydrous glucose to 25 g was prepared. 2.5 g of each mixture were stirred into 50 ml of water in each case. When a solubiliser was present, nitroglycerine precipitation no longer occurred at an elevated temperature, from approximately 60° C. Details are given in the following Table 5.

TABLE 5

|  | Solubiliser | x = nitroglycerine precipitation (formation of droplets) at | | |
|---|---|---|---|---|
|  |  | 24° C. | 60° C. | 70° C. |
| Example 1 | 1,2-propylene glycol | x | x | — |
| 2 | polyethylene glycol (M 300) | x | x | — |
| 3 | N,N—dimethylacetamide | x | x | — |
| 4 | 1,2-propylene glycol-1-n-propylether | x | x | — |
| Comparison Example 1 | omitted | x | x | x |

EXAMPLE 5

(a) Subject to the safety regulations of the explosives industry, 1.6 kg of nitroglycerine were dissolved in from 8 to 10 liters of ether and 1.6 kg of 1,2-propylene glycol were mixed therewith. The solution was then homogeneously mixed with 76.8 kg of glucose in a mixer with the admission of air until the ether had evaporated.

(b) 11.550 kg of the preparation according to (a), added in portions, were dissolved, with stirring, in water previously heated to 70° C., in a boiler. After the solution had cooled, the remainder of, in total, 220 liters of water was added. This solution could then be filled into 10 ml ampoules or 50 ml bottles having pierceable caps.

We claim:
1. An approximately isotonic aqueous nitroglycerine solution, free of ethanol and containing
   (a) approximately 1 mg of nitroglycerine/ml of solution,
   (b) a solubiliser for parenteral administration selected from the group consisting of polyvalent, lower and higher alcohols, lower and higher ether alcohols and amides or organic acids, and
   (c) a nitroglycerine carrier selected from the group consisting of sodium chloride, mannitol, sorbitol, glucose, lactose and levulose and mixtures thereof, and having a weight ratio of nitroglycerine:solubiliser of from 0.1:1 to 10:1, and having an amount of carrier which supplements the total amount of all the substances in an amount of preparation containing approximately 0.1 g of nitroglycerine to the isotonicity equivalent corresponding to approximately 0.90 g of sodium chloride prepared by dissolving a mixture of (a), (b) and (c) in water at a temperature of at least 60° to 100° C.

2. The isotonic aqueous nitroglycerine solution of claim 1 wherein said solubiliser is an alcohol selected from the group consisting of 1,2-propanediol, 1,3-butanediol, glycerine, 1,2-propylene glycol-1-n-propyl ether, 1,2-butylene glycol-1-methyl ether, tetraethylene glycol and polyethylene glycol having an average molecular weight of from 200 to 600.

3. The isotonic aqueous nitroglycerine solution of claim 2 wherein said alcohol is 1,2-propanediol.

4. A preparation according to claim 1, characterized by a weight ratio of nitroglycerine:solubiliser of from 0.2:1 to 5:1.

5. A preparation according to claim 4, characterised by a weight ratio of nitroglycerine:solubiliser of from 0.3:1 to 3:1.

6. A preparation according to claim 5, characterised by a weight ratio of nitroglycerine:solubiliser of from 0.5:1 to 2:1.

7. A preparation according to claim 1 characterised by a molecularly disperse solubiliser, selected from the groups:
   (a) 1,2-propanediol, 1,3-butanediol, and glycerine,
   (b) 1,2-propylene ether, tetraethylene glycol, and polyethylene glycol, with an average molecular weight from 200 to 600,
   (c) isopropylpropylene glycol ether, diethylene glycol dimethyl ether, and tetrahydrofurfuryl methyl ether,
   (d) glycol monoacetate, glycol diacetate, glycol monopropionate, and ethyl lactate,
   (e) lactic acid,
   (f) dimethylformamide, dimethylacetamide, N-(β-hydroxyethyl)-lactamide, and N,N-dimethylmethoxyacetamide,
   (g) isopropylidene glycerol and glycerine formal,
   (h) urea, ethyl urethane, and tetraethylurea, and
   (i) tetrahydrothiophene-1,1-dioxide and colloidally disperse solubilisers selected from the following group: cellulose glycolate; Pluronic; Tetronic; and castor oil/ethylene oxide condensates.

* * * * *